(12) United States Patent
Carmon

(10) Patent No.: US 10,345,137 B2
(45) Date of Patent: Jul. 9, 2019

(54) SYSTEM AND METHOD FOR DETECTING SURFACE VIBRATIONS

(71) Applicant: Guardian Optical Technologies Ltd., Tel-Aviv (IL)

(72) Inventor: Gideon Carmon, Haifa (IL)

(73) Assignee: Guardian Optical Technologies Ltd., Tel-Aviv (IL)

( * ) Notice: Subject to any disclaimer, the term of this patent is extended or adjusted under 35 U.S.C. 154(b) by 0 days.

(21) Appl. No.: 16/049,979

(22) Filed: Jul. 31, 2018

(65) Prior Publication Data

US 2018/0372536 A1   Dec. 27, 2018

Related U.S. Application Data

(63) Continuation of application No. 15/540,049, filed as application No. PCT/IL2015/051255 on Dec. 27, 2015.

(60) Provisional application No. 62/097,061, filed on Dec. 27, 2014.

(51) Int. Cl.

| | |
|---|---|
| *G01H 9/00* | (2006.01) |
| *G02B 27/48* | (2006.01) |
| *G02B 27/10* | (2006.01) |
| *B60N 2/00* | (2006.01) |
| *G01N 21/47* | (2006.01) |
| *G06T 7/20* | (2017.01) |

(52) U.S. Cl.
CPC ............. *G01H 9/00* (2013.01); *B60N 2/002* (2013.01); *G01N 21/4788* (2013.01); *G02B 27/106* (2013.01); *G02B 27/48* (2013.01); *G06T 7/20* (2013.01); *G01N 2021/479* (2013.01)

(58) Field of Classification Search
USPC .......................................... 250/493.1, 504 R
See application file for complete search history.

(56) References Cited

U.S. PATENT DOCUMENTS

| | | | |
|---|---|---|---|
| 4,934,815 | A | 6/1990 | Tai et al. |
| 5,900,935 | A | 5/1999 | Klein et al. |
| 6,188,482 | B1 | 2/2001 | Cloud |
| 7,113,817 | B1 | 9/2006 | Winchester, Jr. et al. |
| 7,978,341 | B2 | 7/2011 | Pouet |
| 8,390,821 | B2 | 3/2013 | Shpunt et al. |

(Continued)

FOREIGN PATENT DOCUMENTS

| | | |
|---|---|---|
| JP | 62081550 | 4/1987 |
| TW | 201344147 | 11/2013 |
| WO | WO 2016/103271 | 6/2016 |

OTHER PUBLICATIONS

Communication Pursuant to Rules 70(2) and 70a(2) EPC dated Aug. 23, 2018 From the European Patent Office Re. Application No. 15872108.4. (1 Page).

(Continued)

*Primary Examiner* — Nicole M Ippolito

(57) ABSTRACT

A system for detecting vibrations from a surface is provided. The system includes a coherent light source for projecting a multi-beam pattern onto the surface and an imaging device for mapping a speckle field generated by each spot formed on the surface by the multi-beam pattern to a unique region of an imaging sensor. The system further includes a processor for processing speckle field information received by the imaging sensor and deriving surface vibration information.

18 Claims, 10 Drawing Sheets

(56) References Cited

U.S. PATENT DOCUMENTS

| | | | |
|---|---|---|---|
| 8,913,247 | B2 | 12/2014 | Rembe et al. |
| 9,217,635 | B2 | 12/2015 | Guetta |
| 9,335,415 | B2 | 5/2016 | Jungwirth |
| 2001/0029416 | A1 | 10/2001 | Breed et al. |
| 2005/0195383 | A1* | 9/2005 | Breed .................... B60N 2/002 356/4.01 |
| 2006/0255689 | A1 | 11/2006 | Deason et al. |
| 2006/0262319 | A1 | 11/2006 | Gatt |
| 2007/0182528 | A1* | 8/2007 | Breed .................... B60Q 9/008 340/435 |
| 2008/0007715 | A1 | 1/2008 | Meldahl et al. |
| 2008/0119993 | A1* | 5/2008 | Breed .................. B60R 19/205 701/46 |
| 2008/0154524 | A1 | 6/2008 | Shirley |
| 2010/0182425 | A1* | 7/2010 | Sakakida ............... B60N 2/002 348/135 |
| 2011/0026783 | A1 | 2/2011 | Fujii et al. |
| 2013/0155195 | A1 | 6/2013 | Zalevsky et al. |
| 2013/0204112 | A1 | 8/2013 | White et al. |
| 2015/0103141 | A1* | 4/2015 | Lee .......................... G01F 1/68 348/43 |
| 2015/0204556 | A1* | 7/2015 | Kusukame ......... B60H 1/00742 165/237 |
| 2018/0266876 | A1 | 9/2018 | Carmon |

OTHER PUBLICATIONS

International Preliminary Report on Patentability dated Jul. 6, 2017 From the International Bureau of WIPO Re. Application No. PCT/IL2015/051255. (9 Pages).

International Search Report and the Written Opinion dated Jun. 27, 2016 From the International Searching Authority Re. Application No. PCT/IL2015/051255.

Invitation to Pay Additional Fees dated Apr. 5, 2016 From the International Searching Authority Re. Application No. PCT/IL2015/051255.

Supplementary European Search Report and the European Search Opinion dated Aug. 6, 2018 From the European Patent Office Re. Application No. 15872108.4. (14 Pages).

Bianchi "Vibration Detection by Observation of Speckle Patterns", Applied Optics, XP001587747, 53(5): 931-936, Published Online Feb. 6, 2014. Para [0932]- [0933].

Pouet et al. "Recent Progress in Multi-Channel Quadrature Interferometer: Demonstration of a Compact Fiberized Architecture", Review of Progress in Quantitative Nondestructive Evaluation, AIP Conference Proceedings, CP894, Oregon, USA, Jul. 30-Aug. 4, 2006, 26(1): 1668-1675, Aug. 2006.

Viasnoff et al. "Multispeckle Diffusing-Wave Spectroscopy: A Tool to Study Slow Relaxation and Time-Dependent Dynamics", Review of Scientific Instruments, 73(6): 2336-2344, Jun. 2002.

Xiang et al. "An Experimental Study on Antipersonnel Landmine Detection Using Acoustic-to-Seismic Coupling", The Journal of the Acoustical Society of America, XP012003344, 113(3): 1333-1341, Mar. 2003. p. 1334.

Official Action dated Nov. 1, 2018 From the US Patent and Trademark Office Re. U.S. Appl. No. 15/540,049. (17 pages).

\* cited by examiner

SYSTEM AND METHOD FOR DETECTING SURFACE VIBRATIONS

RELATED APPLICATIONS

This application is a Continuation of U.S. patent application Ser. No. 15/540,049 filed on Jun. 27, 2017, which is a National Phase of PCT Patent Application No. PCT/IL2015/051255 having International Filing Date of Dec. 27, 2015, which claims the benefit of priority under 35 USC § 119(e) of U.S. Provisional Patent Application No. 62/097,061 filed on Dec. 27, 2014. The contents of the above applications are all incorporated by reference as if fully set forth herein in their entirety.

FIELD AND BACKGROUND OF THE INVENTION

The present invention relates to a system for detecting vibrations from a remote surface and to a method of using same. Embodiments of the present invention relate to a system which utilizes focused speckle imaging to detect vibrations from a remote object or subject.

Devices for measuring surface vibrations of a remote object are known in the art. For example, Laser Doppler Vibrometers (LDV) measure the Doppler shift of a laser beam reflected from a surface to extract the surface velocity and determine surface vibrations.

Devices for measuring speckle patterns generated on a surface are also utilized for identifying surface vibrations of remote objects. Since speckles are characterized by an intensity pattern produced by mutual interference of a set of wave fronts, typical speckles analysis utilizes out-of-focus speckle images in order to maximize the amount of information that can be obtained from this pattern over time. Defocused speckles imaging provides detailed images of the speckles that allows tracking their variation over time to extract surface motion such as rotation, translation and deformation.

Both LDV and speckle analysis approaches suffer from inherent limitations. With LDVs, rough surfaces generate speckles in the reflected light field that generate random noise in the measurement. As a result, surfaces measured by LDVs are usually treated to provide specular reflectance when possible. In addition, LDVs are complicated devices that require an expert for proper operation and utilize laser power which exceeds eye-safety limitations.

With speckle analysis, the camera frame rate limits the frequency band of the extracted information. Although speckle analysis approaches can utilize a high-speed camera (tens of KHz), a large number of frames must be captured, saved in memory and analyzed limiting real-time performance and the size of the measurement time window. In addition, in order to capture meaningful information defocused speckle imaging must cover a relatively large number of pixels. While strong defocusing spreads the laser spot image over multiple pixels, it results in a substantial drop in light intensity which is compensated for by increasing the power of the laser source oftentimes beyond eye safety range.

Although the above solutions can provide quantitative information with respect to a surface, some applications do not require such quantitative information. For example, various applications in modern life require automatic detection of the presence of subjects within an area of interest. In such applications, the main requirements are accurate identification of a subject or subjects without utilizing potentially unsafe radiation and not quantitative information regarding a surface.

Thus, it would be highly advantageous to have, a system which can be used to accurately detect a presence and number of subjects in an environment without subjecting the subjects to potentially harmful radiation.

SUMMARY OF THE INVENTION

According to one aspect of the present invention there is provided a system for detecting vibrations from a surface comprising: (a) a coherent light source for projecting a multi-beam pattern onto the surface; (b) an imaging device for mapping a speckle field generated by each spot formed on the surface by the multi-beam pattern to a unique region of an imaging sensor; and (c) a processor for processing speckle field information received by the imaging sensor and deriving surface vibration information.

According to further features in preferred embodiments of the invention described below, the imaging device is configured for in-focus mapping of each speckle field formed on the surface by the multi-beam pattern.

According to still further features in the described preferred embodiments the light source is configured for projecting a single beam and the system further includes a beam splitter.

According to still further features in the described preferred embodiments the multi-beam pattern is formed from a plurality of non-overlapping non-collimated beams focused onto the surface.

According to still further features in the described preferred embodiments the light source is configured for projecting a plurality of beams at a light wavelength longer than 650 nm.

According to still further features in the described preferred embodiments the multi-beam pattern forms a grid on the surface.

According to still further features in the described preferred embodiments the grid is formed by more than 2 beams.

According to still further features in the described preferred embodiments, the grid covers a field-of-view of up to 180 degrees.

According to still further features in the described preferred embodiment, the processor analyzes a light intensity at each unique region of the imaging sensor to thereby detect speckle dynamics.

According to still further features in the described preferred embodiments the imaging device includes an optical filter for filtering out ambient light.

According to still further features in the described preferred embodiments the imaging sensor includes a photodiode or photodiode array and each speckles field is mapped to 1-100 pixels of the imaging sensor.

According to still further features in the described preferred embodiments the light source is configured for projecting the multi-beam pattern using an optical power of less than 1 milliwatt per beam.

According to still further features in the described preferred embodiments a lens aperture of the light source is selected based on, for example, equations 17-18, 21-22, 27, 30 described hereinbelow.

According to still further features in the described preferred embodiments the light source is configured for projecting the multi-beam pattern to a surface 0.1-15 m away.

According to still further features in the described preferred embodiments the processor is further configured for qualifying the surface based on the surface vibration information.

According to still further features in the described preferred embodiments the system is capable of identifying a human based on the surface vibration information.

According to still further features in the described preferred embodiments the system is configured for mounting inside a vehicle.

According to still further features in the described preferred embodiments the system is capable of communicating a vehicle occupant count to an onboard system of the vehicle.

According to another aspect of the present invention there is provided a system for detecting vibrations from a surface comprising: (a) a coherent light source for projecting a non-collimated beam onto the surface; (b) an imaging device for mapping a speckle field generated by a spot formed on the surface by the non-collimated beam to a unique region of an imaging sensor; and (c) a processor for processing speckle field information received by the imaging sensor and deriving surface vibration information.

According to yet another aspect of the present invention there is provided a system for detecting vibrations from a surface comprising: (a) a coherent light source for projecting a single collimated beam onto the surface; (b) a photodiode for capturing a speckle field generated by a spot formed on the surface by the collimated beam; and (c) a processor for processing speckle field information received by the photodiode and deriving surface vibration information from speckle vibrations at an amplitude of 1 µm to 50 cm and a frequency of 1 Hz-100 KHz.

The present invention successfully addresses the shortcomings of the presently known configurations by providing a system which can be used to detect subjects and objects in an environment without using light radiation that exceeds eye safety guidelines.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE SEVERAL VIEWS OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 6*b* is a logarithmic representation of the plot of FIG. 6*a*.

DESCRIPTION OF THE PREFERRED EMBODIMENTS

Figure 1:
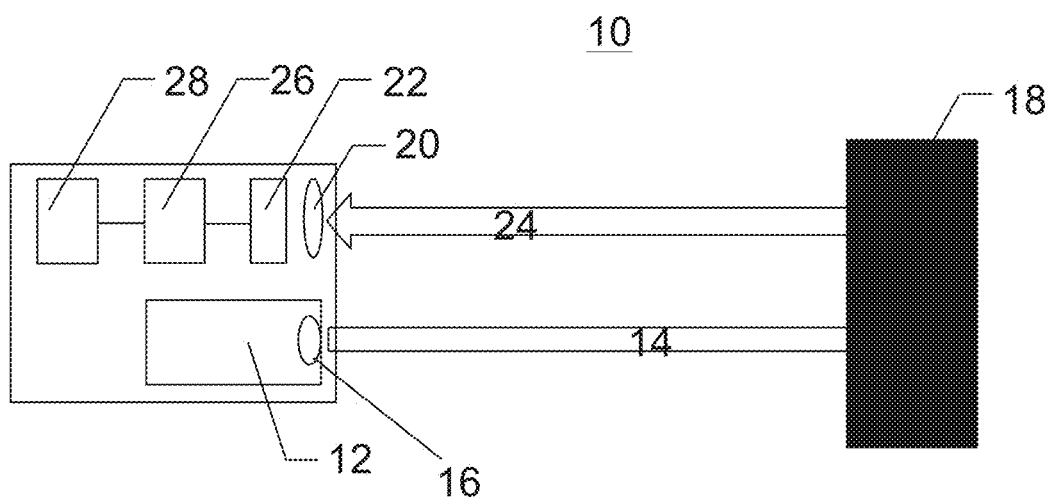
FIG. 1 illustrates one embodiment of an optical setup for monitoring the vibrations of a remote surface constructed in accordance with the teachings of the present invention.

The present invention is of a system which can be used to detect the presence of a subject in an environment or detect changes in an environment related to potentially hazardous situations. Specifically, the present invention can be used to detect the presence of subject in a vehicle in order to provide a vehicle management system with information that can be useful in an event of, for example, an accident. The present invention can be used to detect changes in an environment that relate to the safety and well being of individuals, for example, to detect smoke resulting from a fire in a home.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Approaches for analyzing laser speckle for the purpose of extracting qualitative or quantitative information from a surface of an object are known in the art. Speckle analysis has been described in conjunction with identification of objects (US20080154524); extraction of physiological parameters (US20130204112), biometric authentication (US20110026783), and remote sensing of surface vibrations (Bianchi, Applied Optics, Vol. 53, No. 5, 2014).

Typical speckle analysis approaches utilize out-of-focus speckle images in order to maximize the amount of information that can be obtained from this pattern over time. This is especially true in cases where analysis of a speckle pattern is used for retrieving quantitative information from a surface of an object. In-focus speckle analysis is also known, Bianchi (Ibid) describes a system in which a speckle pattern is focused onto a single pixel detector (photodiode) for the purpose of detecting remote surface vibrations.

While reducing the present invention to practice, the present inventors have devised a speckle analysis system which utilizes eye-safe, low power light radiation (e.g. class I laser) and unique speckle analysis algorithms to detect vibrations from a surface of an object or subject in any environment and in real time. As is further described hereinbelow, the present system is particularly useful for detecting the presence of individuals in a confined space such as an automobile or a home and for detecting environmental hazards such as smoke or an earthquake.

In order to minimize false positives and provide a reliable detection of sedentary or mobile subjects, the present system is configured for detecting surface vibrations resulting from a subject's heart beat and/or breathing.

Thus, according to one aspect of the present invention there is provided a system for detecting vibrations from a surface. The present system can detect vibrations from any remote surface at any distance, including vibrations from inanimate objects and sedentary or mobile subjects such as humans. As is further described hereinunder, the present system is particularly useful for detecting 'physiological vibrations' (skin or clothing/cover vibrations resulting from heart beat or breathing) from humans.

The present system is configured based on the following parameters:

(i) use of a low power light source which projects a non-collimated or collimated coherent light beam or beams which are eye safe (for example, at 830 nm, a narrow collimated beam is limited by an energy level of around 700 µW);

(ii) mapping each speckle field to a unique region of an imaging sensor; and/or (iii) adjusting the aperture of the collecting lens and the beam diameter to optimize speckles dynamics detection in the required amplitudes range.

The present system can be configured in one of several ways in order to provide the above functionality and accurately detect surface vibrations. In a first configuration, the present system includes a coherent light source for projecting a multi-beam pattern onto the surface. Such a coherent light source can be a class I laser emitting at tens of milliwatt, and directed at the diffuser. Each of the multiple beams exiting the diffuser, must be kept below the eye safety limit for the emitted wavelength. For example, at 830 nm, the intensity of the zero order beam must not reach 700 µW. The system also includes an imaging device such as a photodiode array (e.g. CCD) for mapping a speckle field generated by each spot formed on the surface by the multi-beam pattern to a unique region of an imaging sensor. The information captured by the imaging sensor (e.g. light intensity changes) is processed via a processor executing a dedicated algorithm (further described hereinbelow) to derive surface vibration information.

A second configuration of the present system includes a coherent light source for projecting a non-collimated beam onto the surface and an imaging device for mapping a speckle field generated by a spot formed on the surface by the non-collimated beam to a unique region of an imaging sensor. A processor executing a dedicated algorithm then derives surface vibration information from the sensor-captured information.

A third configuration of the present system includes a coherent light source for projecting a single collimated beam onto the surface and a photodiode for capturing a speckle field generated by a spot formed on the surface by the collimated beam. In this configuration, the processor processes speckle field information received by the photodiode to derive surface vibration information from speckle vibrations at an amplitude of 1 µm to 50 cm and a frequency of 1 Hz-100 KHz.

As is mentioned above, the present system employs an algorithm for deriving surface vibration information from changes/shifts in light intensity on the imaging sensor. The algorithm follows the intensity of each spot over time and analyzes its variance. In case of a single spot it analyzes the total intensity collected from that spot, and in case of multiple probed spots, the total intensity of each spot is analyzed separately. It is necessary to differentiate between the variance of the signal originating from the statistical noise of the sensor and the variance originating from a shift in the speckles pattern, indicating a surface motion. For this purpose, a threshold level for the variance is pre-determined in such a way that it remains above the noise level at all times. The threshold is not necessarily a constant in time and can have different values at different external conditions. Once the algorithm detects an increase in the variance above the threshold level it indicates a surface motion at the spot under inspection. The described procedure generates an unfiltered motion detection indication for each spot. To further improve the robustness of the system under false detections, a number of filters are applied to the motion data.

A temporal filter is used for discarding short-term fluctuations, originating from electronic noise or a momentary acoustical shock of the system or environment. Second, in the configuration containing multiple spots, multiple spatial filters are also applied. By analyzing the matrix of motion indications, false detections can be filtered based on object size (by counting the number of positive indications in a given blob of the matrix). If the moving object is much smaller than a human or a pet it is probably generated by a flying bug, or a vibrating cell-phone for example and therefore should not activate a positive detection. In case of a high resolution matrix, the shape of the detected moving object is analyzed for additional filtering of false detections. For example, when two passengers are seating in the back seat on opposite sides, their motion generates movements of the seat which propagate to the empty middle seat. As a consequence, the micro-motion matrix is expected to have randomly positioned dots along the area of the central seat. Comparing shape characteristics such as spatial-frequencies components of a Discrete Cosine Transform for example, or the average radius (distance from center of mass), of a random pattern with those of a human shape provides an efficient tool for differentiation between the two. The present approach can be used, alone or in addition to other algorithms, to provide a reliable occupancy status for the middle seat.

A spatial filter is also used to prevent false detections originating from external noise sources. For example, when a parked car is strongly vibrated by the wind or rain, all of the spots in the matrix are expected to provide positive motion indications. When the spatial filter counts a number of positive indications close to the total number of spots, it prevents the system from providing a false positive detection.

Referring now to the drawings, FIG. 1 illustrates one embodiment of the present system which is referred to herein as system 10.

System 10 includes a laser source 12 emitting a beam 14 at a wavelength λ. The wavelength can be anywhere from the visible to the short infra-red regimes, between 400-2000 nm, depending on the application and sensor type.

Beam 14 is directed via a collimating lens 16 towards a target surface 18. Lens 16 collimates the emitted light and projects a collimated beam. The beam diameter at the target surface is determined by the focal length of lens 16.

Beam 14 impinges upon surface 18 and undergoes diffusive scattering. A collecting lens 20 positioned in front of an imaging sensor 22 (e.g. photodiode or photodiode array) collects backscattered light 24 that reaches lens 20. Lens 20 is covered with a band-pass filter centered at the laser wavelength (e.g. 830 nm) in order to reduce capture of ambient light. Imaging sensor 22 is located close to the imaging plane such that the light energy collected by lens 20 is focused on imaging sensor 22. In the setup shown in FIG. 1, the photocurrent is preferably proportional to the total intensity reaching the aperture of lens 20 and therefore provides a good indication for the collected speckles total intensity.

Imaging sensor 22 does not have to be exactly in the imaging plane. As it is moved away from the focal plane, the size of spot projected upon the photodiode of imaging sensor 22 increases. Imaging sensor 22 can be moved (automatically or manually) until the image of the spot covers one or more photodiodes. This is an important feature for applications where the distance between system 10 and the target can vary significantly. In such cases, there is no need for re-focusing via lens 20 as long as the spot image is smaller than the photodiode.

The light signal captured by imaging sensor 22 is processed by a processor 26 (e.g., a micro-processor such as Amtel ATSAMV71Q21A).

As is described hereinabove, processor 26 executes an algorithm configured for analyzing the variations of the light intensity and detect surface motions.

Based on the processed information, processor 26 determines if surface vibrations are present and the frequency and amplitude of such vibrations are estimated. If the vibration parameters have reached the threshold levels and passed the applied filters, system 10 indicates presence of a subject to a user via interface 28 which can be a display, an audio device (e.g. speaker) and the like. In some configurations of system 10 interface 28 can be part of a vehicle/home management system. Interface 28 can be wired to processor 26 or communicate therewith via a wireless connection (e.g. WiFi, BlueTooth and the like).

The following describes scattered light capture via system 10 in greater detail.

The scattered light field presents random speckles pattern with average speckle size at aperture of lens 20 of:

$$a = \frac{\lambda z}{w} \quad (1)$$

where w is the beam waist at the target 20 and z is the distance from the system to the target.

The speckles field that covers the aperture is integrated by lens 20 onto a focused spot on imaging sensor 22. As a result of the surface vibrations, the speckles pattern projected upon lens 20 varies and the light intensity (I) reaching imaging sensor 22 fluctuates accordingly. The pattern variations are determined by the motion of the surface under inspection, which can be divided into three types of motions: translations, rotations and deformations. Lateral translations generate a shift of the pattern at the same scale as the motion of the surface. Axial translations vary the scaling of the pattern. According to eq. (1), a vibration amplitude of a few microns over a distance of meters has a very weak affect on scaling. Moreover, since the laser spot diameter (w) of a collimated beam also scales linearly with z, the effect of axial vibrations on scaling is further reduced. Surface rotations translates the pattern by $l=2\theta z$ as if the surface was a reflecting mirror. Since pattern translations due to surface rotations are amplified by the distance, it has stronger contribution to the speckles dynamics than both lateral and axial translations.

The last type of surface motion is deformation. Deformation changes the phase distribution of the scattered light and the speckles pattern undergoes random variations that resemble boiling water. In the general case of surface motion, where all three types of motion occur simultaneously, the speckles dynamics is formed of a combination of translations, boiling and scaling.

If the scattering surface is replaced with a transparent cloudy liquid, the scattering particles in the liquid are constantly in motion and therefore the optical paths of the scattered photons vary in time. The observed speckles pattern will therefore be 'strong boiling'. In the light of the above phenomenon, the amplitude of fluctuations of the photocurrent in the system presents a good indicator for surface vibrations.

A statistical model was constructed to quantitatively determine the dependence of the standard deviation of the light intensity reaching the detector, Std(I) in view of the different parameters of the system. Pattern translations due to surface rotation were studied (FIG. 2) and the speckles pattern was modeled with a discrete lattice where each cell has an equal probability to carry intensity s or 0. The cell length a represents the average speckles size. Since this description is valid for the range of small speckles (i.e. where the speckles size is smaller than the lens aperture) the range of large speckles was analyzed separately. Pattern translation of length l was modeled by a discrete shift of the values in the lattice by l/a steps. For simplicity sake, the lens aperture is assumed to be square in size D. The velocity of the speckles pattern v resulting from a surface angular velocity ω is given by v=2ωz. For a given time period between successive data points τ, the translation of the pattern is $l=2\omega z\tau$.

First, the case of l≥D (i.e. the cells of successive frames are uncorrelated) was examined. The intensity I of a single exposure is represented by:

$$I = \sum_{i=1}^{N_s} I_i = \sum_{i=1}^{N_s} s\left(p_i + \frac{1}{2}\right) = \frac{sN_s}{2} + s\sum_{i=1}^{N_s} p_i \quad (2)$$

where $I_i$ is the power level of cell number i and $p_i=\frac{1}{2}$ for a cell with intensity level s and $p_i=-\frac{1}{2}$ for an empty cell, with an equal probability. Averaging the intensity over exposures is derived by:

$$\langle I \rangle = \frac{sN_s}{2} \quad (3)$$

and the average intensity square is derived by:

$$\langle I^2 \rangle = \left\langle \sum_{i=1}^{N_s} \sum_{j=1}^{N_s} I_i I_j \right\rangle = \left\langle \sum_{i=1}^{N_s} \sum_{j=1}^{N_s} s^2 \left(p_i + \frac{1}{2}\right)\left(p_j + \frac{1}{2}\right) \right\rangle = \frac{s^2 N_s^2}{4} + \frac{s^2 N_s}{4}. \quad (4)$$

This enables to uncover the standard deviation, using:

$$Std(I) = \frac{s}{2}\sqrt{N_s}. \quad (5)$$

Introducing the number of speckles $N_s = (D/a)^2$ results in:

$$Std(I) = \frac{s}{2}\left(\frac{D}{a}\right) = \frac{s}{2}\hat{D} \quad \text{for } l > D; \hat{D} > 1. \quad (6)$$

where the normalized aperture diameter $\hat{D}$ was introduced.

Figure 2:
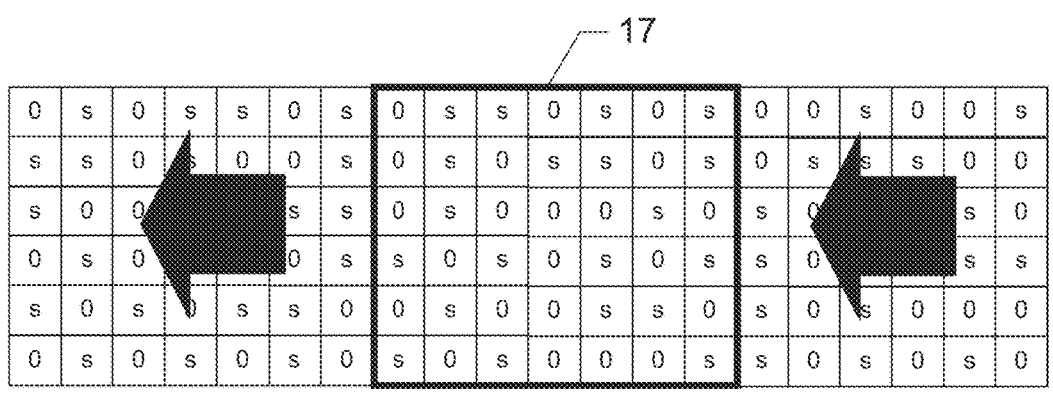
FIG. 2 is a statistical model for analyzing the signal of a speckle filed. The arrows indicate the translation of the pattern along the lens aperture.

The case of slower pattern translations was examined at l<D. In this case, a fraction of the cells is common to pairs of successive frames and only $lD/a^2$ cells are replaced (as is shown in FIG. 2, l/a rows enter the lens surface from the right and all the other cells are found in both frames). To emphasize the correlation between successive frames the standard deviation of $\Delta I^i = I^i - I^{i-1}$ was inspected (the superscript i represents the frame number i).

Calculating the average of $\Delta I^i$ over frames one obtains:

$$\langle \Delta I \rangle = \sum_{j=1}^{N_s} \langle I_j^i - I_j^{i-1} \rangle = \sum_{j=1}^{lD/a^2} \langle I_j^{i-1} - I_j^i \rangle = 0 \quad (7)$$

The average of $(\Delta I)^2$ is given by $$\langle (\Delta I)^2 \rangle = \left\langle \sum_{j=1}^{lD/a^2} \sum_{k=1}^{lD/a^2} (I_j^i - I_j^{i-1})(I_k^i - I_k^{i-1}) \right\rangle = \frac{s^2}{2} \frac{lD}{a^2} \quad (8)$$

and hence $$Std(\Delta I) = \frac{s}{\sqrt{2}}\sqrt{\frac{l}{a}\hat{D}} \quad \text{for } D > l. \quad (9)$$

Replacing the upper limits of the summations in eq. (8) one obtains:

$$Std(\Delta I) = \frac{s}{\sqrt{2}}\hat{D} \quad \text{for } l > D. \quad (10)$$

Using the relation $Std(\Delta I) = \sqrt{2} Std(I)$ derives the following:

$$Std(I) = \frac{s}{2}\sqrt{(l/a)\hat{D}} \quad \text{for } \hat{D} > 1. \quad (11)$$

Next, the range of $\hat{D}<1$ is considered. To model the system under this condition, the aperture size was set a single lattice cell. The speckles in size a>D are represented by squares in the pattern in the size of $n^2$ cells containing equal intensity. Since only a fraction of each speckle is captured by the lens, an effective intensity amplitude $s_{\mathit{eff}} = s\hat{D}^2$ replaces the speckles amplitude s. For the case of l<a the total intensity is constant along a/l frames. Therefore, averaging over N>>a/l frames results in:

$$\langle (\Delta I)^2 \rangle = \frac{1}{N}\sum_{i=1}^{N}(I^i - I^{i-1})^2 = \frac{l}{2a}s_{\mathit{eff}}^2. \quad (12)$$

$$Std(I) = \sqrt{l/a}\,\frac{s_{\mathit{eff}}}{2} = \frac{s}{2}\sqrt{l/a}\,\hat{D}^2 \quad \text{for } a > l; 1 > \hat{D}. \quad (13)$$

For l>a the speckles projected upon the lens aperture vary every frame and therefore:

$$Std(I) = \frac{s}{2}\hat{D}^2 \quad \text{for } l > a; 1 > \hat{D}. \quad (14)$$

The deviations of the light intensity from the average value indicate surface vibrations and is therefore considered as the signal. The relation between the total light intensity reaching the detector (imaging sensor) and the signal level $I_s$ is linear:

$$I_s = \beta I \quad (15)$$

where the pre-factor $\beta$ also includes the intensity loss caused by the various optical surfaces in the imaging portion of the present system. To evaluate the sensitivity of the system, this signal was compared with the fluctuations of the signal resulting from various noise sources. It is therefore desired to set the system parameters in a way that will maximize signal to noise ratio (SNR). For example, in the case of an unamplified photodiode the noise can be modeled as follows:

$$I_N = I_\tau + \alpha\sqrt{I_s} \quad (16)$$

$I_\tau$ is the thermal noise, and $\alpha\sqrt{I_s}$ is the shot noise.

In the case of large pattern amplitudes where l>D one obtains:

$$SNR = \frac{Std(I_s)}{I_N} = \frac{\beta(s/2)\hat{D}^2}{I_\tau + \alpha\sqrt{\beta s/2}\,\hat{D}} \quad \text{for } l > a; 1 > \hat{D} \quad (17)$$

$$SNR = \frac{\beta(s/2)\hat{D}}{I_\tau + \alpha\sqrt{\beta s/2}\,\hat{D}} \quad \text{for } l > D; \hat{D} > 1. \quad (18)$$

In this case the SNR is a monotonously increasing function of $\hat{D}$ such that the more speckles collected by the lens the higher the SNR. However, the SNR has an asymptotic limit of $\sqrt{\beta s/2}/\alpha$. For this reason, increasing the aperture over a certain level will have a negligible contribution to the SNR. To the first order for $\dot{D} \gg I_\tau/\alpha\sqrt{s}$, the deviation of the SNR from the asymptotic limit is:

$$SNR \simeq \frac{\sqrt{\beta s/2}}{\alpha} - \frac{I_\tau}{\alpha^2 \dot{D}} \qquad (19)$$

If, for example, it is required to reach 80% of the SNR limit, eq. (19) shows that $\dot{D}$ has to satisfy:

$$\dot{D}_{80} = 5\frac{I_\tau}{\alpha\sqrt{\beta s/2}} \qquad (20)$$

Next, the case of small amplitude vibrations is analyzed where l<D. In this case the SNR is given by:

$$SNR = \frac{\beta(s/2)\sqrt{l/a}\,\dot{D}^2}{I_\tau + \alpha\sqrt{\beta s/2}\,\dot{D}} \text{ for } l < a; 1 > \dot{D} \qquad (21)$$

$$SNR = \frac{\beta(s/2)\sqrt{(l/a)}\dot{D}}{I_\tau + \alpha\sqrt{\beta s/2}\,\dot{D}} \text{ for } l < D; \dot{D} > 1. \qquad (22)$$

Here the SNR has a global maxima at $$\dot{D}_T = \frac{I_\tau}{\alpha\sqrt{\beta s/2}}.$$

Note that although the SNR does depend on the value of l, the optimal aperture diameter does not. This property is significant in practical applications where the vibration amplitude or frequency and hence l might change over time. Since $\dot{D}_T$ is independent of l, calibrating the aperture to the optimal diameter ensures that the signal will remain optimal in the whole range of D>l>0.

Figure 3:
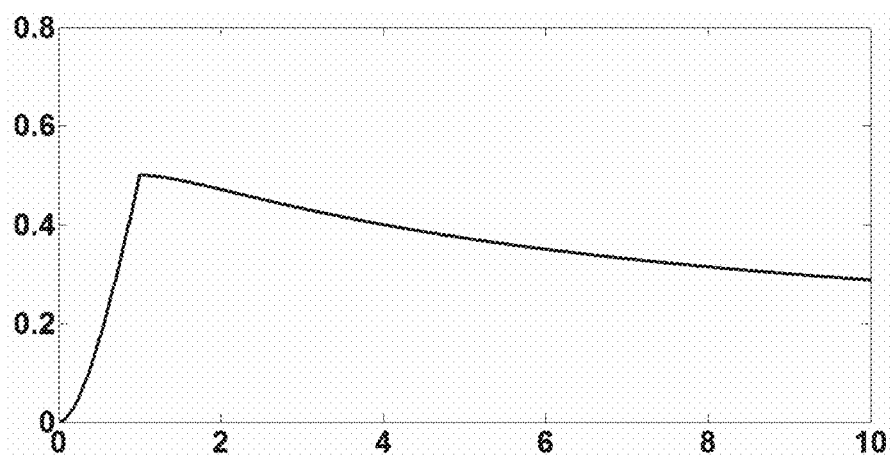
FIG. 3 is a plot of the system SNR vs. the normalized aperture diameter D' for l<D; [eq. (22, 23)] for I_τ=1; α=(l/â)  (¼); β=(√(a/l)) 2/s.

FIG. 3 is a plot of the SNR vs. $\dot{D}$ for D>l, note that for the selected set of parameters in this example the optimal SNR is reached at D=a. In a case where the target vibrations are expected to generate amplitudes in both the D>l and l>D regimes, the optimal aperture should be selected with accordance to the tradeoff between a large aperture which maximizes the SNR at large amplitudes and the small aperture for the small amplitudes regime.

In cases where the vibrating surface undergoes deformations the speckles pattern changes over time. One way to quantify the extent of change in the pattern is by calculating the correlation coefficients between successive frames. On average, the normalized coefficients vary between one, in a case where no changes occurred in the pattern, to zero where the pattern has completely changed. To apply the statistical model on the boiling effect, a random change of intensity is performed in N random cells of the lattice. The new intensity level of each of the N cells is randomly set to 0 or s, regardless of the previous intensity of that cell. The parameter N controls the variation level of the pattern and therefore the decrease in the correlation coefficients. The correlation coefficient of frames i and i−1 is defined as follows:

$$C^i = \frac{\sum_{j=1}^{N_s}(I^i_j - \langle I^i \rangle)(I^{i-1}_j - \langle I^{i-1} \rangle)}{\sqrt{\sum_{j=1}^{N_s}(I^i_j - \langle I^i \rangle)^2}\sqrt{\sum_{j=1}^{N_s}(I^{i-1}_j - \langle I^{i-1} \rangle)^2}}. \qquad (23)$$

To find the relation between the correlation coefficients and N, $C=\langle C^i \rangle$ is calculated for the case of N-replaced cells. The average standard deviation of the intensities is independent of cells replacement as long as the probability distribution remains the same. Therefore averaging the correlation coefficients provides:

$$C = \frac{\left\langle \sum_{j=1}^{N_s}(I^i_j - \langle I^i \rangle)(I^{i-1}_j - \langle I^{i-1} \rangle)\right\rangle}{\sqrt{\sum_{j=1}^{N_s}(I^i_j - \langle I^i \rangle)^2}\sqrt{\sum_{j=1}^{N_s}(I^{i-1}_j - \langle I^{i-1} \rangle)^2}} = \frac{N_s - N}{N_s} = 1 - n \qquad (24)$$

where the normalized parameter $n=N/N_s$ was introduced. Eq. (24) provides a useful transformation from the model parameter n to the measurable quantity C.

Next the standard deviation of ΔI is calculated for the case of N replaced cells:

$$\langle(\Delta I)^2\rangle = \left\langle \sum_{j=1}^{N}\sum_{k=1}^{N}(I^i_j - I^{i-1}_j)(I^i_k - I^{i-1}_k)\right\rangle = \frac{s^2}{2}N \qquad (25)$$

and therefore $$Std(\Delta I) = \frac{s}{\sqrt{2}}\sqrt{n}\dot{D} = \frac{s}{\sqrt{2}}\sqrt{1-C}\dot{D} \qquad (26)$$

The response of the system to a boiling pattern is similar to its response to translations. In the case of strong boiling, where C→0, Std(ΔI) and therefore the SNR is exactly the same as in the case of translation with l>D (eq. (10)). When the translation is larger than D, successive frames are uncorrelated. An important consequence is that there is an upper boundary to the sum of contributions from the translations and boiling to the signal. For partially correlated frames where 1>C>0 the SNR for boiling speckles is found by introducing the pre-factor from eq. (26) in the numerator of eq. (18):

$$SNR = \frac{\beta s/2\sqrt{1-C}\,\dot{D}}{I_\tau + \alpha\sqrt{\beta s/2}\,\dot{D}} \qquad (27)$$

Finally, the general case of a combination of translations and boiling is analyzed. In this case the number of replaced cells is given by the sum of contributions from both effects:

$$N = \frac{lD}{a^2} + \frac{D(D-l)}{a^2}n \qquad (28)$$

Substituting N in the expression for standard deviation in eq. (9) one obtains:

$$Std(\Delta I) = \frac{s}{\sqrt{2}}\sqrt{(l/a)\dot{D} + n\dot{D}(\dot{D} - (l/a))} = \frac{s}{\sqrt{2}}\sqrt{(n\dot{D} + f)^2 - f^2} \quad (29)$$

where $f = \frac{l}{2an}(1-n)$.

The maximal value of the signal is obtained when l=D or n=1, as expected from the analysis for translations and boiling. Dividing the standard deviation by the noise one obtains:

$$SNR = \frac{s/2\beta\sqrt{(n\dot{D} + f(n))^2 - f^2(n)}}{I_\tau + \alpha\sqrt{\beta s/2}\,\dot{D}} \quad (30)$$

The global maxima in this case is found at $$\dot{D}_{T,B} = \frac{I_\tau}{\alpha\sqrt{\beta s/2} - nI_\tau f^{-1}}.$$

Comparing $\dot{D}_{T,B}$ to $\dot{D}_T$ uncovers that the addition of boiling increases the optimal aperture. In the range of weak boiling where $n^2 \ll l/a$ the following applies:

$$\dot{D}_{T,B} \cong \dot{D}_T + nf^{-1} \cong \dot{D}_T + (2a/l)n^2 = \dot{D}_T + (2a/l)(1-C)^2. \quad (31)$$

The second term on the right-hand side, of eq. (31), $(2a/l)(1-C)^2$, mixes the contribution from boiling with the contribution from translations. This indicates that in the presence of boiling the optimal aperture size depends on the translation l.

To test the validity of the results obtained from the statistical model a numerical simulation of the system was constructed. The speckles field is calculated using the Rayleigh-Sommerfeld diffraction formula:

$$U(x, y) = \frac{z}{i\lambda}\int\int_\Sigma e^{i\Phi(\xi,\eta)}\frac{e^{ikr_{01}}}{r_{01}^2}\,d\xi d\eta \quad (32)$$

where $r_{01} = \sqrt{z^2 + (x-\xi)^2 + (y-\eta)^2}$ and $\Phi(\xi, \eta)$ is the phase shift distribution of the reflected field which determined by the surface structure.

Figure 4:
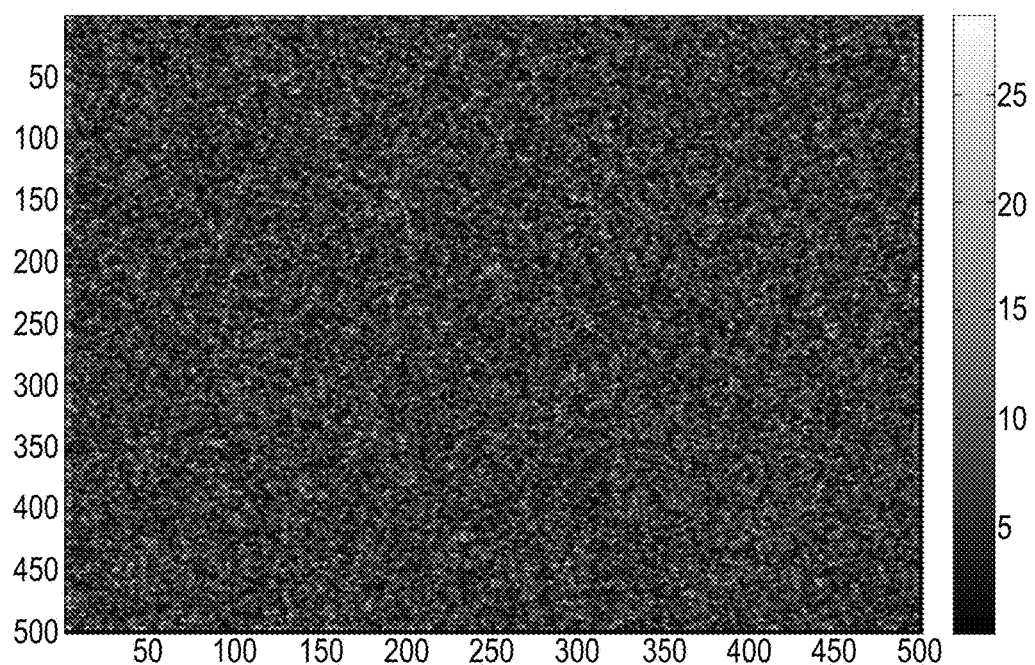
FIG. 4 illustrates the phase distribution at the area covered by the laser spot that was used in the numerical analysis (x and y axes are in units of µm).
Figure 5:
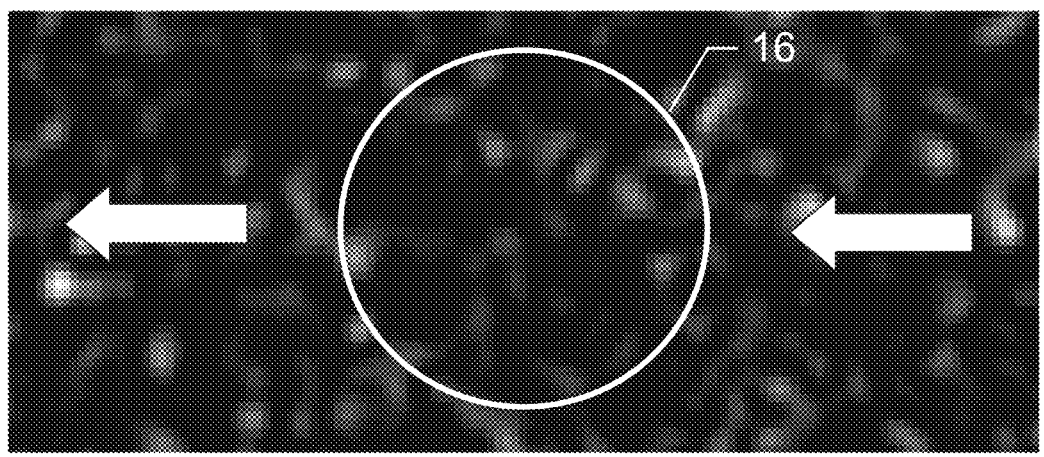
FIG. 5 illustrates a calculated speckles field that is translated over the lens aperture. This field was used for calculating the SNR

In the numerical evaluation of the integral, the parameters were chosen to be $\lambda$=830 nm, z=1 m, and w=0.5 mm. The phase distribution was modeled by a large number of Gaussians with a waist of 1 μm randomly distributed over the integration domain $\Sigma$ (see FIG. 4). A speckles field over a region of 1 m×30 mm at a resolution of 0.5 mm was calculated to provide a large database for averaging. The average speckle size on the plane of the lens aperture is a=2 mm. Lens 20 is simulated by a circular region that is shifted along the generated pattern to address the speckles translations (FIG. 5). In each step the intensity within the circular region was integrated to represent the light intensity reaching imaging sensor 22 at that particular data point.

Figures 6A, 6B:
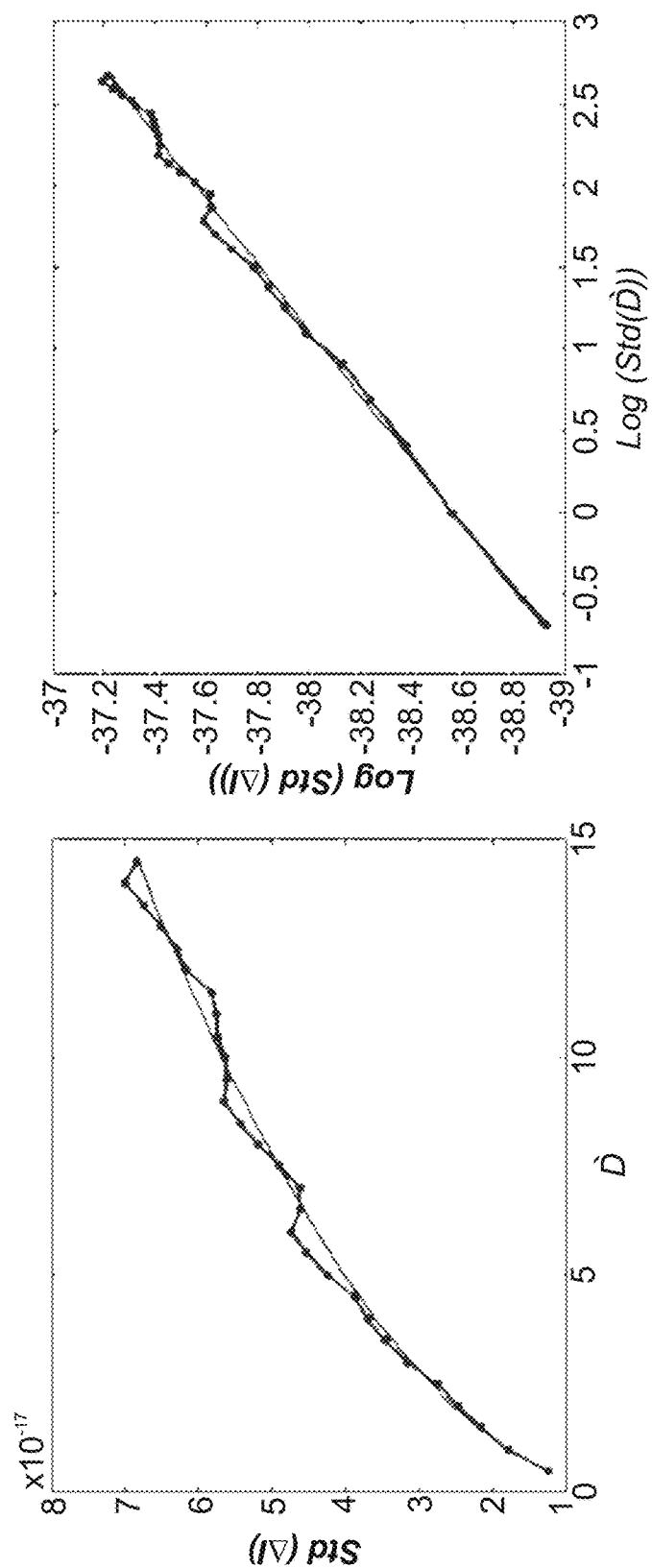
FIGS. 6*a-b* illustrate a plot of Std(ΔI) vs. D' for l=a=2 mm where l<D in the whole range (FIG. 6*a*). Black dots—simulation results, solid line—statistical model result: y=1.79·[ 10 ] ^(−17) √(D').

The aperture of lens 20 was varied between 0.5 mm and 30 mm, where for each aperture the pattern is imaged with a step of l=a=2 mm between successive frames. The results are shown in FIGS. 6A-B. To compare the simulation results with the mathematical model the parameter s is evaluated by the relation $$\langle I \rangle = \frac{s}{2}\dot{D}^2$$

where <I> was estimated by the mean intensity over a region of the calculated speckles field. It was found that s=2.65·10⁻¹⁷. Substituting l=a in eq. (9) shows that the pre-factor of $\sqrt{D}$ is $s/\sqrt{2}$=1.87·10⁻¹⁷. This is comparable with the curve shown in FIG. 6 with a pre-factor of 1.79·10⁻¹⁷.

Figure 7:
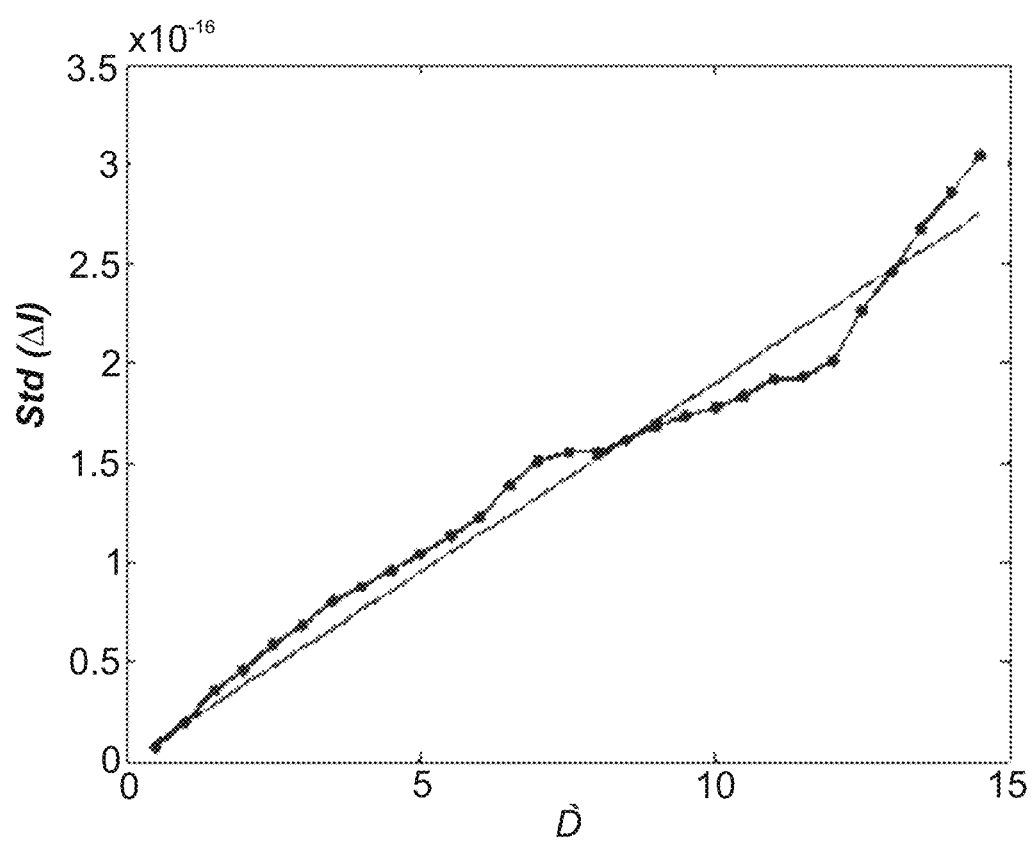
FIG. 7 illustrates a plot of Std(ΔI) vs. D' for l=50 mm>D. Black dots—numerical simulation results. Solid line—statistical model result y=1.9·[ 10 ] ^(−17) D'.

The same procedure was repeated for l=50 mm which lies in the l>D regime. As is shown in FIG. 7, Std($\Delta$I) agrees with the linear relation of eq. (6) with a pre-factor of 1.9·10⁻¹⁷. According to eq. (10) the pre-factor is to be compared with $s/\sqrt{2}$=1.87·10⁻¹⁷. The excellent agreement between the statistical model and the numerical analysis supports the validity of the results obtained from the model constructed herein.

System 10 and the vibration detection algorithm described hereinabove can be configured for use in a variety of applications.

For example, system 10 can be configured for detecting the presence of subjects in a vehicle. Such a system can be used in private cars and public transportation vehicles to prevent the driver from locking the vehicle in case an occupant is present (e.g. baby).

Positioned at the center of the ceiling of a sedan car, the distance to the different seats is typically between 0.5 m and 1.5 m. This is the expected range for the values of z. Since the signal drops with z, it is preferred to optimize the system for the higher values of z, i.e. for z=1.5 m. A near IR laser diode, emitting at 830 nm for example, is preferred for such a use case since it's both invisible to the human eyes (and therefore does not disturb the passengers) and detectable by standard CMOS or CCD sensors. A collimating lens with 1 mm focal length will generate a beam waist of close to 1 mm and with a convergence angle of around 1 mrad. In this case the generated spot has a diameter w of 2.5 mm at 1.5 m. In order for the pattern to cover both the front and back seats a large divergence angle of above 120 degrees is required from the projected pattern. Since typical DOEs can reach only around 40 degrees of divergence, splitting the beam into two or four beams, before it reaches the DOE is required. A different diffuser is placed in front of each of the beams to project the patterns onto the different seats. A standard CMOS detector can be used for sensing. The sensor resolution is not required to reach more than about 4 times the resolution of the pattern. Therefore, a low resolution sensor of 640×480 pixels is sufficient for most applications. A collecting lens with a wide-angle is required to cover a field of view of around 140 deg in both axes. A band-pass optical filter is positioned in front of the camera to block ambient light and allow the system to provide good performance in different lighting conditions. In order to optimize the SNR for any system the relevant equations out of 17-18, 21-22, 27, 30 are to used to determine the lens aperture D. The parameters $\alpha$, $\beta$, $I_s$ needs to be measured for the specific sensor and optical elements in a setup. The speckles size s can be found from eq. (1). In the current example s=0.5 mm. In the discussed use-case, one should expect to have various speckles dynamic modes. Large-amplitude translations resulting from moving passengers and small-amplitude translations generated by the breathing and heart-beats of static passengers (sleeping for example). In addition, when using a near infra-red wavelength boiling is also expected to occur at spots that shine the naked skin on the face or arms. The different modes must be taken into account where choosing the relevant equations for optimizing the system. In this case, the tradeoff is between eq. (27, 30) describing boiling speckles and eq. (17-18, 21-22) representing moving speckles. Another degree of freedom in the system is the spot diameter, which is determined by the collimating lens and the laser diode. Varying the focal length can bring the system closer to the optimum instead or in addition to the control over the lens aperture.

A vehicle-specific system can be installed in the vehicle ceiling (for example near the passengers lights and the air conditioner opening, or above the passageway) above each seat and aimed towards the center of the seat (see FIGS. 9a-b), the sensor will detect the presence of a passenger based on the vibrations of his clothes. In case the IR laser hits the naked skin, it penetrates into the blood where it is scattered and the resulting speckles pattern is strongly 'boiling'. Adjusting the sensor parameters accordingly enables measuring of strong signals from both the clothes and the skin.

The approach of measuring micro-vibrations to detect human presence as taught by the present invention is highly accurate and reliable and enables automatic filtering-out of vibration of the vehicle (caused by driving or external sources such as wind, rain, passing vehicles etc.). The latter is due to the fact that system 10 is fixedly attached to the vehicle and vibrates therewith and as such, it will only measure motion relative to the sensor and not measure any motion of surfaces not occupied by passengers.

In contrast, prior art approach for detecting human presence via acoustical microphones are negatively affected by ambient sounds which can be orders of magnitudes higher than that generated by a subject (especially when sleeping). In addition, ambient sounds are diverse and completely unpredictable. Therefore the approach of acoustical detection of humans in a vehicle is not practical for sleeping passengers.

Another unique feature of the present system is the ability to detect presence of subjects even when covered (with a blanket or a hat covering the face). Since micro-vibrations are carried from the body to the cover, detection of cover vibration in a physiological range indicates presence of a subject. This feature cannot be provided by detection systems that employ computer vision sensors, where the shape of the body or face is searched in the images, and a covered person is completely undetectable.

Figure 8:
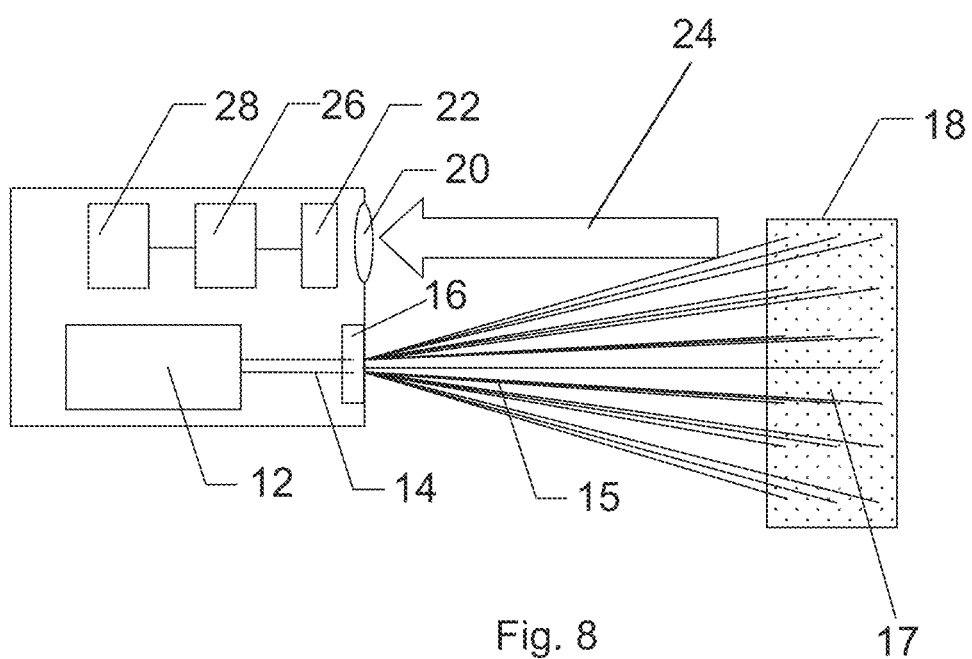
FIG. 8 is an embodiment of the present system configured for detecting subjects inside a vehicle.

FIG. 8 illustrates one embodiment of system 10 which can be used for detection of driver/passengers in a vehicle.

System 10 includes a laser light source 12 fitted with a diffraction grating 26. Grating 26, which is also referred to herein as DOE (diffractive optical element), splits beam 14 into a diffraction pattern 15 that is approximately determined by the Fourier Transform of grating 26. For example, a pattern of dots positioned along a line is generated by a grating with the shape of a comb.

Using an appropriate DOE, pattern 15 projected onto target 18 (e.g. skin or clothes of passenger) is a two-dimensional matrix of laser spots 17. Projected matrix 17 is selected such that it covers the entire field of view of imaging sensor (CCD or CMOS) when collected by lens 20 while maintaining a cell length smaller than the smallest object to be monitored. The cell length is the product of the distance to the target and the angular separation of adjacent the dots in the matrix, determined by the structure of the DOE.

Lens 20 collects a focused image of the scene and projects it onto sensor 22. The spot size on the image plane is given by Mw, where w is the spot size on the object and M is the magnification of the imaging lens. The size of each matrix spot should cover one or a few pixels, such that $Mw \cong p$, where p is the pixel size. The image of each spot represents the total intensity scattered from the corresponding region on the target and collected by lens 20. Therefore, the total intensity of each spot in the image can be replaced with the photocurrent obtained from imaging sensor 22 as is describe above with respect to FIG. 1.

In the embodiment of FIG. 8, the frames captured by sensor 22 contain data from multiple spots projected onto target 18. The standard deviations of the intensity in each pixel containing a matrix spot represents the vibrations at this point. A simple algorithm that calculates the standard deviations of a stack of frames and compares the results with a pre-defined threshold can provide the vibrations detection. For example, the threshold can be set to be equal three times the noise level. Calibrating the system against a static target allows measuring the average standard deviation originated by the sensor noise alone. This value can be used for an estimation of the noise level, and therefore for the threshold.

The aperture of lens 20 as well as other system parameters such as the focal length of lens 16 and the pixel size on the sensor are selected suitable for vehicle detection of passengers, as described in the example above.

The light signal captured by imaging sensor 22 is processed by a processor 26 (e.g., a micro-processor such as Amtel ATSAMV71Q21A).

Processor 26 executes an algorithm configured for vehicle detection of passengers, using the principles described above.

Based on the processed information, processor 26 determines if passengers are present, the number of passengers and their state (awake/asleep). This information is relayed (wired or wirelessly) a vehicle management system 28 which utilizes the information for various safety applications such as airbag suppression, airbag deployment optimization, unbuckled seat-belt warning, etc.

System 10 shown in FIG. 8 can be installed in any vehicle having any internal volume including passenger cars and public transport vehicles such as trains and busses.

Figure 9A:
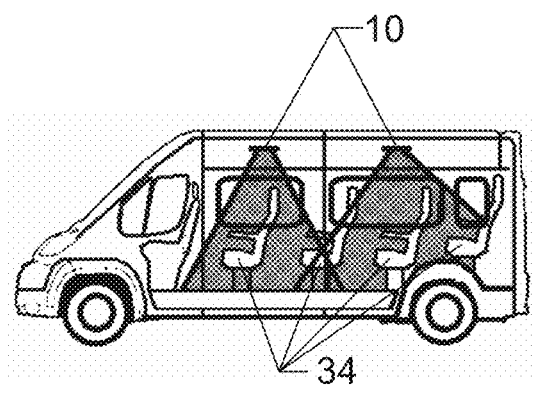
FIGS. 9*a-b* illustrate an embodiment of the system of FIG. 8 mounted in a vehicle showing the coverage of the system in a side (FIG. 9*a*) and top (FIG. 9*b*) views of the vehicle.
Figure 9B:
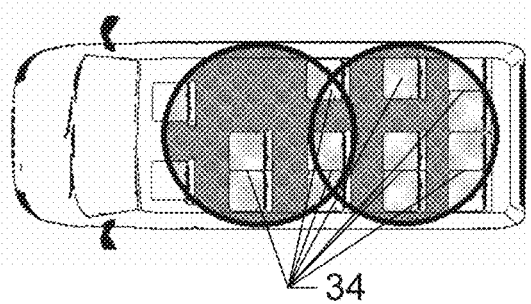

FIGS. 9a-b illustrate a vehicle (van) fitted with two units of system 10 installed against the roof liner of the vehicle. A private vehicle (sedan) can be covered via a single unit of system 10 mounted against the roof liner.

These units of system 10 cover all passenger seats 34 in the vehicle with a matrix of laser dots separated by ~15 cm and employ a lens 20 with the appropriate field of view (e.g. around 140 deg diagonal, depending on the specific car model) to enable collection of speckles fields projected from passengers occupying some or all of seats 34.

Such an installation of system 10 ensures reliable detection of sleeping or awake passengers, covered or exposed, within the whole volume of the car.

System 10 is particularly useful for detecting babies in a car. In hot weather, baby seats can be covered by a canopy to block sunlight exposure. The vibrations generated by the baby's breathings and heart beat are transferred through the baby seat to the canopy and are detectable by system 10.

System 10 can also be used to detect presence of subject in non-vehicle environments including homes, offices, outdoor venues and the like. Such detection can have a variety of applications.

Automatic power switches are used to turn the lights and air conditioner off in offices when they are left empty. System 10 can be used to scan a room and provide an indication for such a switch.

System 10 can also be used for actuating automatic doors which open when an approaching human is detected or for actuating elevator doors.

System 10 can also be used to differentiate between humans and objects. For example, a system 10 that detects the presence of passengers in various seats in a car and monitors the status of each seat belt can be used to remind passengers to buckle their seat belt.

The present system can also be configured for detecting a hazard in an environment. For example, a hazard that can potentially be deleterious to humans or animals such as fire. A system 10 setup positioned on the ceiling of a standard room (16 m$^2$) with a wide angle lens can cover the entire room. Splitting the emitted beam with one or two glass beam-splitters and positioning a DOE in front of each beam, generates a pattern wide enough to cover the whole room as well. The scattering of the projected light by smoke particles generates boiling effect in the speckles pattern. The boiling intensity, that is, the rate of the random change of the speckles, is determined by the type and density of the smoke particles. Equations 27 and 30 provide the signal level for all the range of boiling intensity and there the optimal system parameters for smoke detection can be found. The first layer of the smoke detection algorithm is similar to the human detection algorithm. The standard deviation of each spot is compared with a pre-determined threshold to provide a micro-motion layer indicating which spot is scattered by smoke (or a moving surface) and which does not. The second algorithmic layer is applied on the micro-motion layer, and mainly aimed to differentiate smoke from moving surfaced. Both temporal and spatial filters are applied for that purpose. The temporal filter is applied on each spot separately and is aimed to reveal patterns which are unique for smoke dynamics. The spatial filter utilizes a number of the characteristics of smoke. First, the volume containing the smoke both moves and expands with time as smoke is generated. Second, smoke climbs upwards in a closed room or sucked towards the openings in an open room. Therefore, the micro-motion layer is expected to show similar dynamics when smoke is present in the probed room. Note that both examples of smoke dynamics are unique for smoke and are not expected to occur by the presence of persons. A system calibration after installation in a room adds another layer of protection. Depending on the specific room, there are usually a finite number of positions where fire is likely to occur (e.g. electrical sockets). Marking the high-risk positions in the frame improves the algorithm by allowing it to give higher weight for detections in one of the volumes around each position, when analyzing the situation in the room.

As used herein the term "about" refers to ±10%.

Additional objects, advantages, and novel features of the present invention will become apparent to one ordinarily skilled in the art upon examination of the following examples, which are not intended to be limiting.

EXAMPLES

Reference is now made to the following examples, which together with the above descriptions, illustrate the invention in a non limiting fashion.

Motion Detection Performance

A prototype system was assembled based on an Aptina MT9V034 monochrome CMOS sensor. A lens with a focal length of 6 mm and an F# of 1.8 was used for imaging. The video feed from the sensor was captured on a personal computer via a USB cable at 60 Hz. The projected pattern was generated with a laser diode emitting at 532 nm and a collimating lens with a focal length of 2 mm. Since the imaging lens has a fixed aperture, to control D̂ the collimating lens was shifted along the optical axis to change the beam convergence angle and therefore the spot size on the target. A three-axis stage was positioned in front of the system 1 meter away. A step motor with an accuracy of 300 nm was attached to the stage and controlled via a computer. The motor steps generate an axial motion. Axial motion was not detected at all by the system since the speckles pattern is insensitive to such motion. To generate a surface tilt, a paper tape was stretched between the stage and the basis, such that the paper was slightly tilted with the motion of the stage, with a negligible deformation of the paper (<0.1%). The resulting tilt angle α generated by a motor step of 1 μm is α<50 μRad. The motor was programmed to perform steps in one direction with amplitudes between 1 μm and 0.5 mm. The recorded frames were analyzed with the described algorithm and generated a motion-detection signal.

Figure 10:
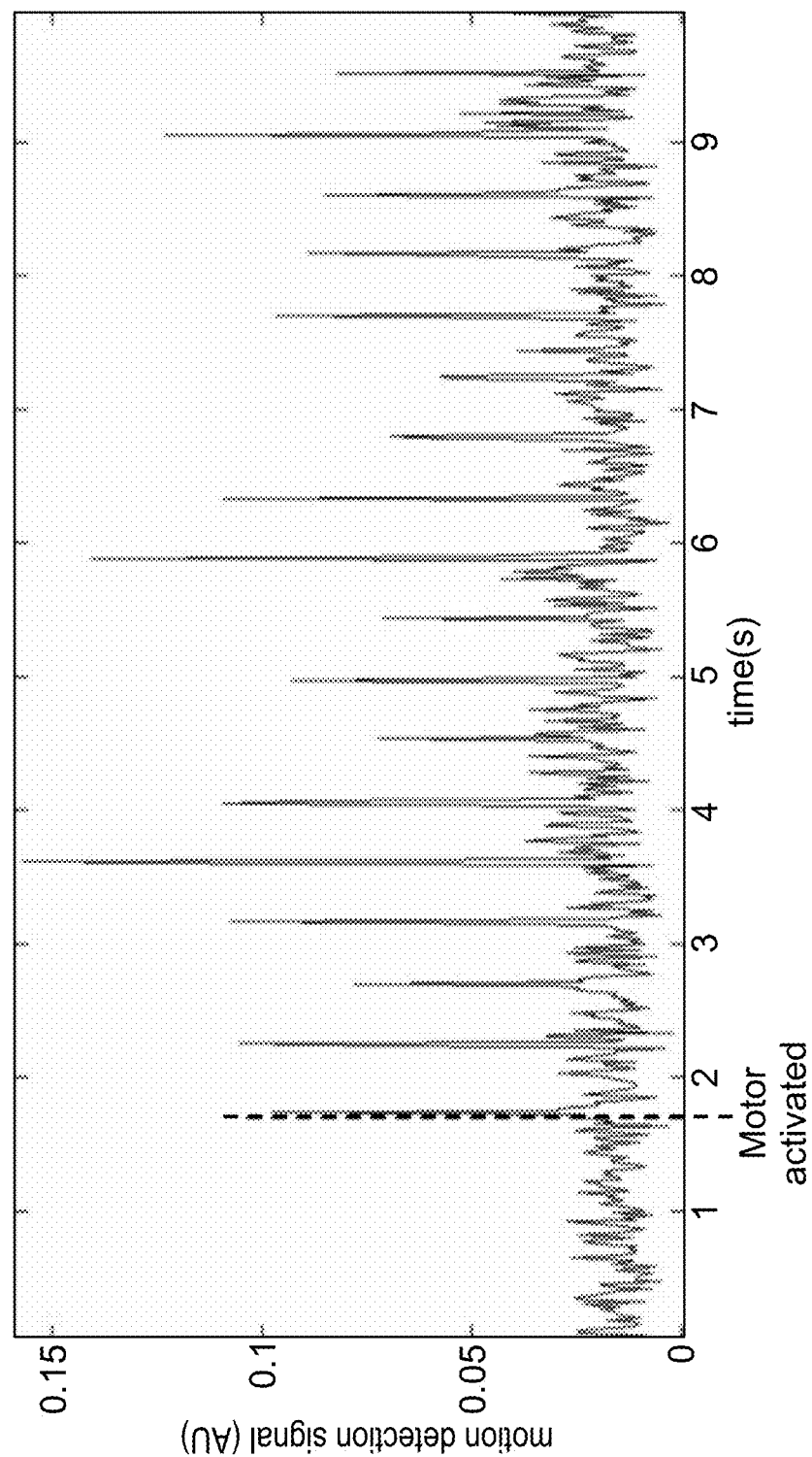
FIG. 10 is a graph illustrating the motion detection performance of the present system.

The results for a step size of 1 μm at a frequency of 2 Hz are shown in FIG. 10. A clear detection of the micro-motions was observed for steps in all the range; the SNR was between 5 and 10 for all the measurements. Next the system was tested on a static human. The laser spot was aimed at different parts of the target body. While the target remains as static as possible, a video feed was recorded for each position. It was found that strong micro-motion signal was detected from all of the different body parts, including the hands, legs and feet. Moreover, strong signal was obtained from the seat itself the target was sitting on. When the target positioned his hands on the table in front of him, strong signals were detected from the whole area of the table surface. Next, A DOE was positioned in front of the emitted beam to provide a pattern of a rectangular lattice of 5×5 dots with a separation angle of 8 degrees in both axes. The different system components where assembled on a rigid surface and a band-pass optical filter was positioned in front of the system to block ambient light. The system was attached on a metal bar that was positioned between the floor and ceiling of a sedan car. Using a fish-eye lens (around 160 degrees diagonal) for imaging the whole cabin was covered by the system. Passengers were seated in the different seats and the projected pattern was aimed towards all 5 seats to collect data. The micro-motion signals from empty and occupied seats were compared for system evaluation. The results show large difference between the signal level of occupied seats and empty seats as long as the passengers are static. When a passenger is moving on the back seat, motion signals are received from the whole seat. To prevent false positive detections an additional algorithmic layer is required. For example, an algorithm was applied to the video feeds and enabled to differentiate between a single passenger that moves the whole seat and a seat containing two passengers. Another test was performed in a car with a baby that was seated in a baby seat. Two different baby seats were positioned in the passenger seat and in the back seat in forward-facing and backward-facing positions. A 5 months old baby was seated in different positions with the sun-shade of the baby-seat pulled down to prevent a line-of-sight with the baby. It was found that a while the baby was moving inside the seat strong micro-motion signals were detected from the baby seat itself and from the back seat of the car. When a sleeping baby was monitored, strong signals were received from different spots on the baby seat, allowing the detection of presence. An additional test was performed to verify the robustness of the system against vibrations of the car from external sources such as wind, rain, passing vehicles etc. For that purpose the sensor monitored the cabin while the car was strongly shaken from the outside. Since the sensor was strongly attached to the body of the car it moved along with it and detected only little relative motion with the seats. The signals arriving from empty seats of a shaking car were lower than those originated by occupied seats, allowing the system to differentiate between the two scenarios and provide reliable occupancy indications for each seat separately.

A different test was performed to evaluate the capability of the system to detect cigarette smoke. The system was positioned in a closed room in distanced 1 m away from a burning cigarette. The video feed was recorded while the collimating lens was scanned along the optical axis to vary the speckles size. It was found that the effect of the smoke on the speckles pattern is detectible by the present system.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A system adapted for monitoring a passenger compartment of a vehicle, comprising:
   an image sensor adapted to detect infra-red light;
   a processor adapted to receive outputs of the image sensor via a wired or wireless connection with the image sensor;
   a wide angle lens mounted in front of the image sensor and having a wide field of view; and
   a mount adapted to connect the image sensor and the wide angle lens to the passenger compartment such that the wide field of view covers at least part of each of a plurality of seats in the passenger compartment so as to allow the processor to detect at least one human parameter in each of the plurality of seats based on an analysis of the outputs of the image sensor.

2. The system of claim 1, wherein the processor adapted to detect a presence or an absence of the human in each of the plurality of seats based on an analysis of outputs of the image sensor.

3. The system of claim 1, wherein analysis is includes analysis of vibrations detected in areas covering the plurality of seats.

4. The system of claim 1, wherein the mount is adapted to connected to a reflecting mirror of the vehicle.

5. The system of claim 1, wherein the at least one human parameter comprises a member of a group consisting of occupancy, mass, age, height, pose, and gaze direction.

6. The system of claim 1, further comprising a front upper console connected to the mount.

7. The system of claim 1, wherein the processor is further adapted to extract a depth map from the outputs; wherein the at least one human parameter is detected using the depth map.

8. The system of claim 1, wherein the wide field of view of at least 140 degrees diagonal.

9. The system of claim 1, wherein the plurality of seats are all of the seats of the passenger compartment.

10. The system of claim 1, further comprising a coherent light source for projecting a light pattern onto each of the plurality of seats; wherein the processor is further adapted to extract parameters based on an analysis of the light pattern in the outputs of the image sensor.

11. The system of claim 10, wherein said coherent light source projects a plurality of beams at a light wavelength longer than 650 nm.

12. The system of claim 1, wherein the processor is further adapted to extract parameters based on an analysis of speckle field information from the outputs of the image sensor to detect heart beat and/or breathing of at least one passenger seated in the plurality of seats.

13. The system of claim 12, wherein the speckle field information is derived by mapping a speckle field generated by a spot formed on by a coherent light source.

14. The system of claim 1, wherein the wide angle lens is a fish-eye lens.

15. A method for monitoring a passenger compartment of a vehicle, comprising:
    using an image sensor for capturing infra-red light reflected from a plurality of seats in the passenger compartment, the infra-red light is captured using an image sensor having wide angle lens and physically mounted on the passenger compartment such that a wide field of view of the wide angle lens covers at least part of each of a plurality of seats in the passenger compartment;
    using a processor for receiving outputs of the image sensor via a wired or wireless connection with the image sensor; and
    using the processor for detecting at least one human parameter in each of the plurality of seats by an analysis of outputs of the image sensor.

16. The method of claim 15, wherein the infra-red light is reflected from a plurality of different spots projected on each of the plurality of seats.

17. The method of claim 15, further comprising projecting a light pattern onto each of the plurality of seats; wherein the detecting is based on parameters extracted from an analysis of the light pattern in the outputs of the image sensor.

18. A computer product for monitoring a passenger compartment of a vehicle, comprising:
    a non transitory computer readable storage medium storing program instructions for:
    using an image sensor for capturing infra-red light reflected from a plurality of seats in the passenger compartment, the infra-red light is captured using an image sensor having wide angle lens and physically mounted on the passenger compartment such that a wide field of view of the wide angle lens covers at least part of each of a plurality of seats in the passenger compartment;

using a processor for receiving outputs of the image sensor via a wired or wireless connection with the image sensor; and using the processor detecting at least one human parameter in each of the plurality of seats by an analysis of outputs of the image sensor.

\* \* \* \* \*